US000001149H

United States Statutory Invention Registration [19]

[11] Reg. Number: H1149

Wyman et al.

[43] Published: Mar. 2, 1993

[54] HIGH SOLIDS FERMENTATION REACTOR

[75] Inventors: Charles E. Wyman, Lakewood; Karel Grohmann; Michael E. Himmel, both of Littleton; Christopher J. Richard, Lakewood, all of Colo.

[73] Assignee: The United States of America as represented by the United States Department of Energy, Washington, D.C.

[21] Appl. No.: 310,557

[22] Filed: Feb. 15, 1989

[51] Int. Cl.[5] ..... C12M 1/02
[52] U.S. Cl. ..... 435/316
[58] Field of Search ..... 435/284–287, 435/316; 422/184

[56] References Cited

U.S. PATENT DOCUMENTS

| | | | |
|---|---|---|---|
| D. 286,293 | 10/1986 | Germain . | |
| 493,342 | 3/1893 | Rach | 435/316 |
| 2,474,833 | 7/1949 | Eweson | 422/287 |
| 3,666,242 | 5/1972 | Fifer . | |
| 4,302,546 | 11/1981 | Schlichting, Jr. | 422/184 |

FOREIGN PATENT DOCUMENTS 60-150821 8/1985 Japan .

OTHER PUBLICATIONS

M. Z. Lowenstein, SERI Anaerobic Digestion Program 1984 Annual Report, SERI/PR-231-2691, SERI, Golden, Colo. (1985).

T. Goldberg, B. Bjergbaek, E. Djernaes, & A. Mouritzen, *An Anaerobic Digester for Continual High Solid Loading: The Bio-Funnel (A Radially Expanding, Overflow Digester)*, International Gas Research Conference (1981).

S. Ghosh, Solid-Phase Methane Fermentation of Solid Wastes, Eleventh American Society of Mechanical Engineers National Waste Processing Conference, Orlando, Fla. (1984).

R. P. Goebel, *High Solids Anaerobic Digester for Rural Use*, U.S. DOE Technical Report No. De-FG-03-81SF11613, (1983).

Yow-Ming Lind, *Coupled High Solids Fermentation and Anaerobic Filtration of Cellulosic Residues*, Ph.D. Thesis, Michigan State University, pp. 73-86 and 190-194, (1983).

Snell Environmental Group, Inc. (SEG), Rapid Methane Generation from Solid Waste, U.S. DOE Technical Report No. DE-FG02-81R510329, (1983).

R. Legrand, *Continuous Anaerobic Digestion of High Solids Biomass: Modeling and Experiments*, U.S. DOE Project No. DE-AC02-76ET20051, vol. II, (1980).

*Primary Examiner*—Richard D. Lovering
*Assistant Examiner*—Joseph D. Anthony
*Attorney, Agent, or Firm*—Ken Richardson; James W. Weinberger

[57] ABSTRACT

A fermentation reactor and method for fermentation of materials having greater than about 10% solids. The reactor includes a rotatable shaft along the central axis, the shaft including rods extending outwardly to mix the materials. The reactor and method are useful for anaerobic digestion of municipal solid wastes to produce methane, for production of commodity chemicals from organic materials, and for microbial fermentation processes.

9 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIG. 1
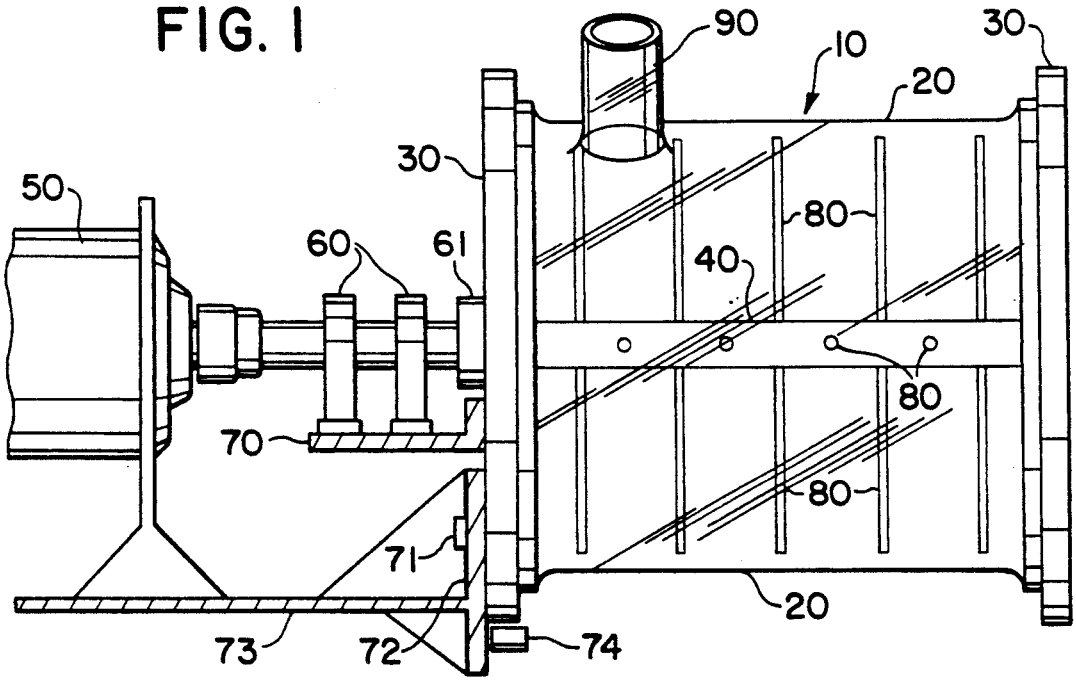
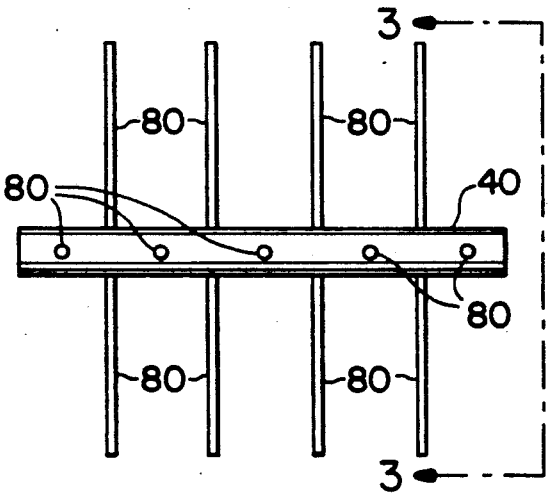
FIG. 2
FIG. 3
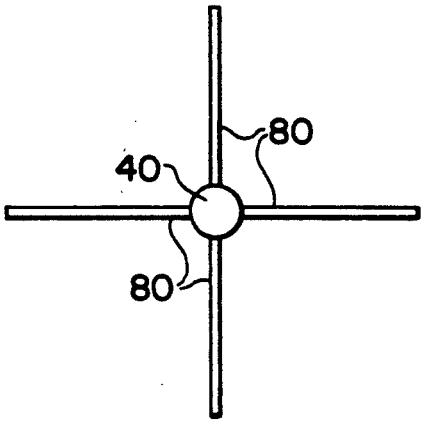

HIGH SOLIDS FERMENTATION REACTOR

CONTRACTUAL ORIGIN OF THE INVENTION

The United States Government has rights in this invention pursuant to Contract No. DE-AC02-83CH10093 between the U.S. Department of Energy and the Solar Energy Research Institute, a Division of the Midwest Research Institute.

BACKGROUND OF THE INVENTION

The present invention relates to improved anaerobic fermentation processes for the digestion of solid waste slurries conducted at high solids concentrations and to improved fermentation reactors for use in said processes comprising mixing means.

Anaerobic digestion of municipal solid waste (MSW) couples the potential of producing considerable energy (methane) with the simultaneous reduction in organic-waste disposal problems by a much less energy-intensive process than conventional aerobic processing methods. However, several key issues must still be overcome before the methane produced is economically competitive with conventional sources of natural gas. Because the value of methane produced is relatively low, the anaerobic process must be rather simple in design, require little energy to operate, and maintain high gas production rates.

Economic evaluations of anaerobic digestion for production of gas from MSW, B. Goodman et al. *Anaerobic Digestion for Energy Production*, SERI/SP-231-2624 (1985), show that receptor capital costs are a significant economic burden because of the large reactor volumes required in current anaerobic processes operated normally at lower solid levels (3%–5%). However, the inventors have determined that if solids levels could be increased significantly (above 10%), gas production rates per reactor volume would increase as well, thereby lowering reactor costs.

Solid biomasses absorb water so readily that a slurry of biomass in water from about 10% to 15% solids concentration and higher more closely resembles a damp solid than a pumpable slurry. Thus, the viscous slurry that results cannot be mixed in conventional fermentation equipment, and water is typically added to lower the viscosity sufficiently (to 10% solid levels or less) that mechanical agitation is possible. Alternatively, the system may be operated without mixing, but inhomogeneities develop that result in lower conversion rates, thereby negating much, if not all, of the gain of high solids operation.

Historically, research on higher solids anaerobic fermentation has focused on the single charge (batch), non-mixed reactor concept, generally with recirculation of effluent S. Ghosh *Solid-Phase Methane Fermentation of Solid Wastes*, Eleventh American Society of Mechanical Engineers: National Waste Processing Conference, Orlando, Fla. (1984); R. P. Goebel, *High Solids Anaerobic Digester for Rural Use*, U.S. DOE Technical Report No. DE-FG03-81 SF-11613 (1983); Y. M. Lin *Coupled High Solids Fermentation and Anaerobic Filtration of Cellulosic Residues*, Ph.D. Thesis, Michigan State University (1983); Snell Environmental Group (SEG), *Rapid Methane Generation from Solid Waste*, U.S. DOE Technical Report No. DE-FG02-81R510329 (1983); R. LeGrand et al., *Continuous Anaerobic Digestion of High Solids Biomass: Modeling and Experiments*, U.S. DOE Project No. DE-AC-02-76ET20051, Vol. II (1980); S. J. Hall et al. *Mesophilic Anaerobic Digestion of High Solids Cattle Waste in a Packed Bed Digester*, J. Agric. Eng. Res. 32:153–162 (1985); W. J. Wujcik and W. J. Jewell *Biotechnology and Bioengineering Symposium*, No. 10, pp. 43–65 (1980).

With non-mixed systems, rates of gas production are generally much slower than in liquid, mixed system, M. Z. Lowenstein *SERI Anaerobic Digestion Program*, 1984 *Annual Report*, SERI/PR-231-2691; Snell Environmental Group, supra; W. J. Wujcik and W. J. Jewell, supra. The retention time of solids required to effect a near complete digestion of the substrate in non-mixed liquid systems is on the order of months for mesophilic temperatures and of weeks for thermophilic operation.

Other workers have investigated two approaches to mixed higher solids fermentation. T. Goldberg et al. *An Anaerobic Digester for Continual High Solid Loading: The Bio-Funnel*, International Gas Research Conference, Aarhus County, Denmark (1981), consisted of a funnel-shaped digester wherein materials loaded at about 21% solids were reduced to about 13% solids after passing upward through the bottom of the funnel and spilling over the top. Agitation of the material occurred as the material expanded in going toward the top of the funnel. Lowenstein supra attained solids feeding as high as 10% solids within the digester in a modified continuous stirred tank reactor (CSTR).

Applicants have surmised that if even higher solids concentrations could be efficiently processed, the reactor volume could be reduced significantly, and the economics of anaerobic digestion of MSW to produce methane, and the fermentation of other organic substrates, such as biomass to produce ethanol, might improve.

Available kinetic data suggest that production rates should increase with solids concentration in the reactor, V. J. Srivastava et al., *Aquatic Plants for Water Treatment and Resource Recovery*, (K. R. Reedy et al., eds.) Part 4:713 (1987). Applicants therefore hypothesized that if these data were substantiated, a decreased reactor volume would be possible for higher solids concentrations while maintaining the same solids loading rate and retention time. The higher conversion rates achievable at higher concentrations of solids will decrease the reactor volume even more.

A reactor design allowing high solids material to be well mixed would increase the interaction of substrate, microorganisms, and metabolic intermediates. Prior reactors for mixing and operation at solids level of 9% or greater have resulted in problems with material movement caused by substrate bridging, scum formation and zones of non-mixing within the reactors when the solids levels fall above 10%.

It has thus been shown that prior to this invention a substantial need for an economical apparatus for digestion of solid wastes and biomass existed, and that the fermentation industry had not been able to produce such an apparatus, nor to conduct high solids digestion in a reliably efficient manner.

The fermentation reactor of this invention is a significantly different concept that those used in high solids fermentation research by other investigators (Lowenstein, supra, and Goldberg et al., supra). This reactor, used in batch or continuous operation, provides adequate mixing of high solids materials having concentrations in the reactor of about 10% to 100%, i.e., damp solids rather than pumpable slurries.

Devices similar to the reactor of this invention have not been found to be available to the fermentation industry, although a search through the patent literature discloses several devices that have certain similarities to this reactor in non-analogous arts. U.S. Pat. No. Des. 8,004 to Reynolds for a *Feather Renovator*, discloses a hand-operated cylindrical container having a shaft equipped with non-symmetrically disposed rods, presumably for beating feathers. This patent does not disclose or suggest automatic rotation or any other special configurations useful for fermentation. U.S. Pat. No. Des. 286,293 to Germain for *Design for Spreader Agitator*, discloses a shaft equipped with short agitator members broader at the bottom than at the top, which appear to be designed for intensive, high sheer mixing that would destroy microorganisms or enzymes. The shortness of the agitator members with respect to the diameter of the shaft would cause inadequate mixing in a reactor large enough to have sufficient reaction volume, or in a smaller reactor, would provide insufficient reaction volume. U.S. Pat. No. 1,725,868 to Kenyon for *Machine for Conditioining Gravel*, shows a device that has too large a shaft diameter with respect to the vessel diameter to be useful in fermentation reactions, and that would require excessive power to operate. U.S. Pat. No. 3,012,977 to Wilson et al. for *Method for Making Synthetic Resin Foams*, depicts a device that has a vertical rather than a horizontal shaft with broad paddles. This device is designed for use with liquid chemical reaction systems, not with solids fermentation processes. U.S. Pat. No. 3,666,242 to Fifer for *Waste Treatment Apparatus and Circulation Unit Therefor*, discloses a stationary vertical circulation unit for aerobic digestion processes, with a lift impeller in the center. Japanese Patent Disclosure 60-150821 to Chisso Corp. for *Horizontal single shaft cylindrical vessel stirring device—partic. for polymers such as polyethylene, polypropylene or polybutene*, depicts a device designed with broad, flat paddles as the end of its mixing members, such that *tacky polymer flows smoothly around the shaft and is stirred so as to wash around the shaft.* None of these patents disclose a reaction vessel with mixing members suitable for fermentation of high solids materials.

SUMMARY OF THE INVENTION

Accordingly, it is a general object of the present invention to provide a smaller, more efficient fermentation reactor for the digestion of solid wastes and other solid substrates.

It is also an object of this invention to provide a fermentation method and reactor for digesting wastes and other solid substrates at greater than about 10% solids concentration.

It is also an object of this invention to provide a fermentation reactor that has mixing means capable of achieving substantial uniformity of distribution of substrates, microorganisms, and enzymes comprising a rotatable shaft equipped with rigidly attached mixing members.

Additional objects, advantages, and novel features of the present invention shall be set forth in part in the description that follows, and in part will become apparent to persons skilled in the art upon examination of the following or may be learned by the practice of the invention. The objects and advantages of the invention may be realized and attained by means of the instrumentalities and in combination particularly pointed out in the appended claims.

To achieve the foregoing and other objects and in accordance with the present invention as embodied and broadly described herein, the method and apparatus of this invention involves the use of a high solids fermentation reactor designed for fermentation of materials comprising greater than about 10% solids. The reactor comprises a vessel having an automatically rotatable shaft along the central axis thereof, said shaft being equipped with rigidly attached mixing members capable of stirring said materials.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In the drawings:

FIG. 1 is a side view of the preferred MSW anaerobic digester of this invention equipped with staggered rows of rod-shaped mixing members, the rows disposed at 90° angles with respect to each other.

FIG. 2 is a side view of the shaft and mixing members of FIG. 1 without the surrounding reaction vessel.

FIG. 3 is an end view of the shaft and mixing members seen along cross-section line 3—3 of FIG. 2.

DETAILED DESCRIPTION OF THE PREFERRED EMBODIMENTS

Figure 4:
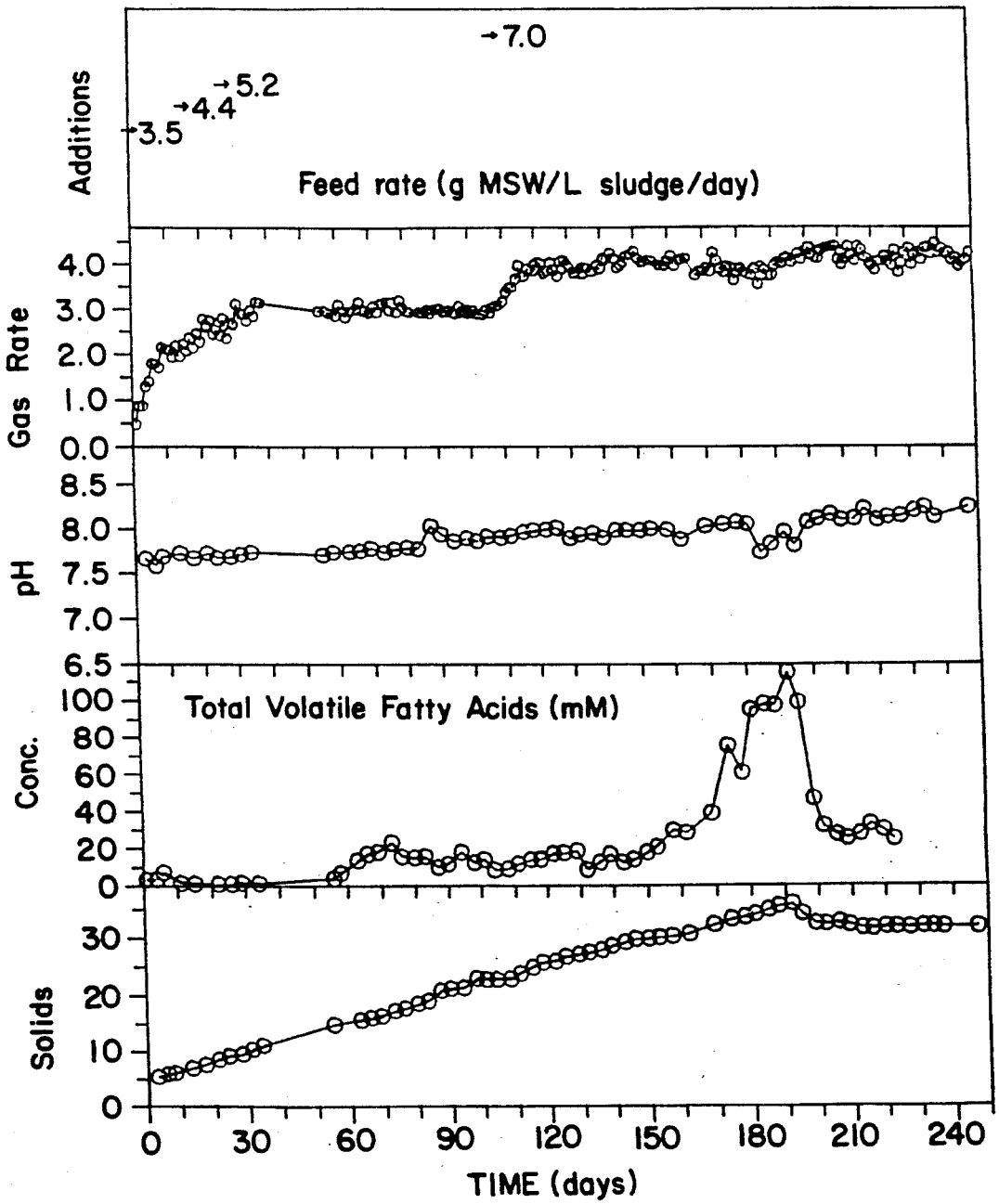
FIG. 4 is a graph showing gas production rate in the anaerobic digestion of MSW over time during a 240-day period compared with variations in pH, solids concentration, and total volatile fatty acids over the same period.

FIG. 1 shows a fermentation reactor of the present invention, generally indicated by the reference numeral 10. The reactor 10 is designed for fermentation of materials that have greater than about 10% solids concentration, preferably between about 10% and about 65% concentration.

The reactor 10 may be of any convenient size useful for economic operation of the fermentation process being conducted. Large reactors with capacities of about 20 L or more may be used to produce fuel products; whereas small reactors having capacities of only a few liters are useful for fermentation processes to obtain valuable expression products of microorganisms.

Moreover, the fermentation reactor 10 can be an aerobic or anaerobic reactor. Preferably, the reactor 10 is an anaerobic digester for solids such as manure, sewage or MSW; more preferably, for the digestion of MSW to produce methane.

It can also be a fermenter for digestion of organic materials to produce primary fermentation products or commodity chemicals such as ethanol, organic acids, or ketones, as is known in the art, or fermenter for the production of products such as expression products of genetically engineered or selected bacteria or fungus or other microorganisms (e.g., for the production of penicillin or other medicines).

The preferred solid concentration will be dictated by the particular material being treated and the product being produced, and can be optimized by known methods without undue experimentation. The reactor 10 of this invention is designed especially for use at high solids concentrations at which conventional fermentation apparatuses that provide mixing means are inoperable or so inefficient as to be economically unfeasible.

Generally, such conventional apparatuses cannot provide efficient mixing at solids concentrations above about 10%, but as is known to those skilled in the art, this may vary with other properties of the material such as viscosity and uniformity.

Also, as is known in the art, the maximum solids concentration at which the process may be efficiently operated may vary. In the case of anaerobic digestion of MSW to produce methane and similar processes, the upper limit is the highest solids concentration at which the bacteria used in the digestion process are viable. Solids concentrations of about 25% to about 45% for MSW are preferred.

The reactor 10 consists of a hollow cylindrical vessel defined by outer circumferential walls 20 and front and rear walls of caps 30. The front wall, also called the headplate, is attached to a seal 61 which, in the preferred embodiment, is a stuffing box seal.

The reactor 10 includes an automatically rotatable shaft 40. The shaft 40 runs through a center axis of the vessel and is connected to an automatic means such as a motor 50 for rotating the shaft 40, as will be more fully explained hereinafter. The shaft 40 is supported by bearing 60 on a first support plate 70 mounted to the headplate. Latching bolts 71 secure a second support plate 72 from the framework 73 to the vessel headplate during routine operation. When these bolts are removed, the vessel can be rotated about the axis of shaft 10 for easy materials recovery.

The shaft 10 is equipped with rigidly attached mixing members or rods 80 capable of mixing the materials to be fermented so as to provide a uniformity of contact between the material in the reactor 10. A round circumference for the reactor vessel is preferred, so as to provide a uniformity of contact between the mixing members 80 and the material in the reactor 10. More preferably, the reactor vessel is cylindrical. The vessel may be disposed at any angle, but horizontal is preferable such that the shaft 40 in the center (a previously mentioned) extends horizontally.

The mixing members 80 may be straight or wing-shaped blades. They may be equipped with angled projections that serve as wipers or scoops. Preferably, the mixing members 80 are all the same size and shape, although if the vessel is barrel-shaped, funnel-shaped, or otherwise non-cylindrical, the mixing members 80 can be sized to accommodate the vessel shape.

The mixing members extend from the shaft 40 toward the vessel and are attached in staggered rows along the length of the shaft 40 at an angle to each other, preferably at 90% angles, but also possibly at 120°, 180°, or other angles. They need not extend the entire length of the shaft 40, but preferably extend along the entire length so as to maximize contact with the material being processed. The mixing members, when configured as blades 80, may be continuous or discontinuous.

An extreme embodiment of the discontinuous blades is the preferred embodiment depicted in FIGS. 1–3. Rod-shaped mixing members 80 are used and spaced along the length of the shaft, disposed in staggered rows at 180°, 120°, 90° or other intervals between rows. Preferably, the mixing members 80 are disposed at 90° intervals between rows and staggered such that the rod-shaped mixing blade members 80 in each row are spaced along the length of the shaft 40 halfway between the rods in adjacent rows, and such that in alternate rows the rods are parallel to each other.

The discontinuous mixing blade or members 80 may be spaced along the shaft 40 at any suitable distance from each other that will provide adequate mixing without undue power requirements. In a preferred embodiment using a 20 L reactor, rod-shaped members 80 having a cross section diameter of about ¼ to ½ in. are used, and the rod members 80 are axially spaced about 2½ to 3 in. apart to provide good mixing.

Such mixing members 80 move through the material being stirred to create a furrow into which more material is then pushed by subsequent action of the next row of mixing members. Preferably, the mixing members 80 are sufficiently small so as to pick up no substantial amounts of the material. When the fermenter 10 is less than completely full, some material may be picked up on the mixing members 80; however, it is preferred that the mixing members 80 allow the material picked up to be dropped onto the mass of material in the digester.

It is not necessary that the mixing members 80 extend the entire distance from the shaft 40 to the inner portions of the walls 20 of the mixing vessel. However, for most applications it is preferred that they extend to within a short distance required for clearance of said walls. This clearance distance is not critical, but it should be small enough so as to prevent buildup of unmixed material along the vessel walls.

As previously described, the rod-shaped members or discontinuous blades 80 may be cylindrical in form (circular in cross section), or they may be rectangular or any other convenient shape, so long as they provide sufficient mixing to allow operation of the process at economically efficient rates, which will be more fully described below. In a preferred embodiment, an economically efficient rate of five substrate volumes of gaseous product per day from the digestion of MSW has been obtained by the applicants. Power requirements for mixing with the chosen mixing member configuration should also be considered. Selection of suitable configurations may be made using methods described herein.

The mixing members 80 may be of any material that has the necessary strength, durability, and resistance to corrosion by the fermenter contents. For some uses, stainless steel is preferred. It is preferred that the mixing members 80 be rigidly attached to the shaft 40 so as not to be displaced by the material being mixed. When the material being digested is of a sticky or viscous consistency, as high-solid-concentration MSW tends to be, it is also useful to provide mixing members 80 that are stick-resistant (e.g., coated with teflon( so as to prevent buildup on the mixing members of the material being mixed. In such cases, it is also preferred that the shaft 40 be stick-resistant.

Referring now to the motor 50, it is driven by electric, hydraulic or pneumatic power. As previously described, the motor 50 rotates the shaft 40 that bears the mixing members 80 to provide the reactor 10 with a continuous mixing capability.

Speed of rotation of the shaft 40 is adjustable to achieve maximum efficiency of production with minimum power output, in a well-known manner to those skilled in the art and as taught herein. Preferably, the speed is about 1.5 rpm. Rotation may be continuous or discontinuous, but preferably is continuous and slow rather than discontinuous and rapid.

A port 90 for feed introduction and material removal is provided. This is equipped with a ball valve (not shown). In the preferred embodiment, feed is introduced through the port 90 with a plunger assembly, and material is removed through the port 90 by rotating the vessel so that the port 90 is on the bottom, such that the material can drop into a receiver vessel connected to the port 90.

Referring now to the first support plate 70, the fact that the plate 70 is mounted to the headplate 30 instead of the frame means that when the vessel is rotated, the shaft 40, held by the bearings 60, and the seal 61 are kept in alignment such that the seal 61 is not damaged. A gas outlet, such as a hose barb (not shown) is provided at the top of the vessel.

It will now be appreciated that the invention also provides an improved fermentation method that conducts the process at greater than about 10% solids concentration and provides continuous mechanical agitation thereto. Preferably, the solids concentration is between about 10% and about 65%, and for digestion of MSW is between about 25% and about 45%. The method may be a batch method or a continuous-feed method, but the latter is preferred.

The applicants have found that starting the reactor 10 at solids concentrations below about 10% and gradually building up the solids concentrations to optimal concentrations greater than this by slowly adding solids is most effective for anaerobic digestion. The rate at which solids are built up is dependent on achieving a balanced digestion process and is especially important in cases where a consortium of microorganisms are required for digestion, and digestion occurs in stages, with each stage dependent on the conditions produced by the preceding stage. Techniques for optimizing this balance as taught herein with respect to digestion of MSW to produce methane may be adapted and modified by those skilled in the art without undue experimentation to achieve optimal balance and long-term efficiency of other processes.

It will be apparent that monitoring and adjustment of pH and other internal conditions may also be important to achieving an efficient, balanced, continuous, long-term fermentation process with respect to the preferred method for digestion of materials to produce fuel products. With respect to methane production, pH is maintained between about 7 and about 8. For ethanol production from organic materials, pH is preferably kept between about 4 and about 5. Those skilled in the art will be able to adapt the methods described herein to other processes without undue experimentation.

In operation, as shown in FIG. 4, reactor 10 is filled with MSW at a concentration less than 10% solids and the solids concentration is gradually built up by addition of progressively higher solids feed material to a concentration of about 35% at about 180 days, leveling off to about 32% thereafter.

As shown in the top portion of FIG. 4, initial feed was loaded at 3.5 g/L of reactor contents per day until about day 14, when the feed rate was adjusted to 4.4 g/L per day. The reactor contents for this experiment (4.6 L), were deliberately kept low so that the action of the mixing apparatus could be observed, including the shaft 40 and rods 80 thereon. Higher reactor contents up to preferred contents known in the art (e.g., about 85% to 90%) are contemplated for general operation of the apparatus. The initial feed rate is kept up until about day 26, at which time 5.2 g/L feed was added per day. After about day 26, 5.2 g/L sludge per day was added until about day 105, when 7.0 g/L feed was added.

As shown in the middle graph of FIG. 4, pH in the reactor 10 was maintained between about 7.5 and 8.0. In this preferred embodiment, pH was controlled in this experiment solely by adjustment of solids concentration. However, as is known in the art, pH may be maintained by conventional means in the art; e.g., by adding urea, potassium hydroxide, or sodium carbonate. Sodium carbonate addition is preferred as being less inhibitory to the microbial population. The pH should not be allowed to fall below about 7 for the anaerobic digestion system of intent here.

Immediately below the pH graph, the total volatile fatty acids composition of the digester is depicted. The high levels of acids shown at about day 180, corresponding with the maximum solids concentration and the slight drop shown in the pH graph, indicated inhibition of the population of acetogens and methanogens in the digester sludge, possibly as a result of too rapid a rate of increase in solids concentration. This condition was corrected by lowering the solids concentration from 35% to about 32%, whereupon fatty acid concentration fell to acceptable levels with a corresponding rise in pH.

Gas production in occupied volumes per day is depicted in the second graph from the top of FIG. 4. Gas production rose steadily with solids concentration and leveled off at about 4 v/d. At this writing, gas production at the rate of 5 occupied v/d has been achieved.

During operation of the fermenter 10, the shaft 40 and mixing rods 80 were continuously rotated at about 1.5 rpm. The shaft 40 and rods 80 are teflon-coated to minimize sticking of the material in the digester, which is about the consistency of papier mache. Material that sticks to the rods 80 tends to fall off during the upward swing of the rods.

The shaft 40 with attached rods 80 is turned by mechanical means 50 such that the rods 80 rotate around the shaft and move circumferentially around the cylindrical vessel 20, thereby mixing the contents. As the shaft 40 turns, the rods 80 positioned initially at 12 o'clock will move clockwise or counterclockwise downward until they contact the solids being fermented. Continued turning will force the rods 80 through the solid material, causing the solid material to move sideways, much like the action of a rake moving through soil in a garden. With continued motion, the rods 80 will lift out of he material on the other side, returning to the starting position to repeat the action. When the described rod 80 is at the 12 o'clock position, other rods will be moving through the solid material at other positions along the length of the shaft 40. This action will force material back into the region swept by the rod 80 pictured, thereby filling the furrow created by the first rod. The combined action of a number of such rods 80, acting in an alternating manner on the solid material as the shaft 40 turns, is to move the material back and forth and thoroughly mix the reactor contents.

The advantage to the reactor 10 described is that it requires very low power to mix the reactor contents because it gently moves the high solids material to one side as it rotates without picking up appreciable amounts of the material. Furthermore, the agitator shaft 40 and mixing blades 80 can be turned at slow rates, thereby requiring very low power inputs while still preventing the formation of nonhomogeneous regions in the fermenting material. The agitator can also mix low concentrations of material well, thus providing the capability to mix the material even if reaction results in thinning caused by loss of solids. This agitator can also be applied to batch, semi-batch, or continuous processing in which fermentation of high solids concentrations would be favorable.

A further description of the invention is given and optimization of parameters is taught by the following examples.

EXAMPLES

EXAMPLE 1

High Solids Reactor Design and Construction

The reactor was a cylindrical glass vessel 10 which was positioned with a horizontal axis as shown in FIG. 1. The cylinder was capped at each end and a shaft 40 was positioned horizontally along the cylinder axis between the centers of the two end caps 30. Several ports were added to the glass vessel for feed addition, sample removal, gas removal, and liquid addition. Mixing was achieved with one of several different blade configurations attached to the horizontal shaft. Shaft rotation was provided by a low speed, high torque, hydraulic motor 50 (5 piston, 35 horsepower maximum). The hydraulic motor was powered by a custom-fabricated hydraulic power station (10 horsepower). The hydraulic motor speed was controlled by Vickers temperature compensated flow control valves. The shaft seal was fabricated as a stuffing box-type seal using teflon rope packing and provided a liquid/gas tight seal even at fractional rpm operation of the reactor.

Several blade configurations were designed, fabricated, and tested for mixing ability and horsepower requirements. The final blade configuration chosen for fermentation studies (90° rods 80) was teflon-coated to reduce biomass buildup and metal pitting from anaerobic reactions.

The glass vessel was modified with two ¾-in.ports for liquid introduction and gas removal. A 2-in. ball valve was attached with couplings to the 2-in. glass port with beaded lip at the top of the glass vessel and was used for sampling the contents of the reactor. Several glass receiving vessels were constructed, which coupled to the outside of the 2-in. ball valve and allowed gassing of the receiver vessel with oxygen-free nitrogen gas before sampling. A solids addition unit was fabricated using a 2-in. plunger to add dry MSW feed to the reactor through the 2-in. ball valve. Two gassing ports were installed on the solids feeder to allow outgassing of the dry MSW before addition to the reactor.

EXAMPLE 2

Horsepower Determinations

Determination of horsepower was calculated by standard methods from the specific motor volumetric throughput and monitored hydraulic back-pressure. Horsepower requirements were determined for several blade configurations with various milled materials.

EXAMPLE 3

High Solids Reactor Operation

In anaerobic fermentation studies, the 90° rod or the rake blade (having a 90° angle in the rod at the end thereof) was chosen. The speed of mixing was maintained at approximately 1.5 rpm. Several different methods of initiating the fermentation were used and are described below. In general, the 20-L vessel was outgassed with oxygen-free nitrogen gas prior to the introduction of inoculum to remove air. The gas production was monitored using one of the ports on the glass vessel connected to calibrated water displacement reservoirs. Sludge was removed from the reactor on a daily or bi-daily basis for determination of pH, volatile organic acid analysis, and microbial observation.

EXAMPLE 4

Enhanced Acetogen/Methanogen Digester

A 2-L New Brunswick Multigen fermenter (1.5 L working volume) was used for production of an enhanced acetogen/methanogen consortium. The reactor was magnetically stirred and temperature controlled at 27° C. using heat tape (Breskheat), Omega temperature controller (model 601), and K-type thermocouple. A liquid feedstock was used for constant feed addition and pH control. The liquid feed contained yeast extract, 8 g/L; $K_2HPO_4$, 50 mM; and 10× trace mineral solution, 10 mL/L (Balch et al. [1979] Microbial. Rev. 43:260–296), as well as the following organic acids: formic, 18 mM; acetic, 766 mM; propionic, 76 mM; n-butyric, 102 mM; n-valeric, 4 mM; iso-valeric; 2 mM; and lactic, 182 mM. The final pH of the organic acid/-nutrient solution was approximately 4.2. A Markson (model 6300) pH/ORP controller with gel-filled electrode monitored the reactor pH and added the organic acid solution when the pH approached 7.4 using a masterflex pump (Cole-Parmer). Effluent from the reactor (about 500 mL) was removed weekly and cells concentrated by centrifugation under a oxygen-free gas phase in 500-mL plastic centrifuge bottles at 5000 rpm for 30 min. and 4° C., using a Beckman centrifuge (model RC-5B) and GSA rotor. The cell pellets were stored at 4° C. until use.

EXAMPLE 5

Digester Inoculum

Sludge from a 7-L working volume anaerobic digester (Chemap) served as inoculum for the high solids reactors. The digester was maintained on a 20-d retention time and temperature controlled at 37° C. using heat tape around the glass reactor and an Omega temperature controller (model 601) with K-type thermocouple. The reactor was fed a processed, densified, MSW from Thief River Falls, Minn., which was knife milled using a 1-mm rejection screen. The reactor was batch fed daily a 5% solids mixture with addition of a nutrient supplement to the milled MSW. The nutrient supplement contained the following components per liter of distilled water; yeast extract (Difco) 8 g, $K_2HPO_4$ 8.7 lg, 10× trace mineral solution 10 mL (Balch et al., supra). The final pH of the nutrient solution was adjusted to 7.5.

EXAMPLE 6

High Solids Sludge Analysis

Levels of volatile organic acids (C1–C5) iso and normal acids were determined by gas-liquid chromatography (GLC). A model 5840A gas chromatograph (Hewlett-Packard, Palo Alto, Calif.), equipped with a flame ionization detector, a model 7672A autosampler, and a model 5840A integrator (all from Hewlett-Packard), was used. The glass column (6 ft×2 mm) was packed with Supelco 60/80 Carbopack C/0.3% Carbowax 20M/0.1% $H_3PO_4$. The injection port temperature and detector were maintained at 190° C. The oven temperature was maintained at 120° C. Nitrogen at a flow rate of 50 mL/min was used as the carrier gas. The experimental samples were calibrated against a quantitative standard (Supelco) with each run. Experimental samples were prepared for analysis by centrifugation to remove suspended solids in 1.5-mL microcentrifuge tubes in a microcentrifuge (Eppendorf) at room temperature for 15 min. The clarified samples were acidified by addition (1:1) with 1% v/v formic acid. Finally, the samples were loaded into autosampler vials, crimp caps were attached and the vials were loaded in the autosampler for analysis.

Analysis of non-volatile organic acids in digester sludge effluent was accomplished by high performance liquid chromatography (HPLC). Experimental samples were clarified by centrifugation as described above with final removal of particulates by passage through a 0.2 micron Acrodisc disposable syringe filter (Gelman #4418). The samples were made 0.01 N with sulfuric acid and loaded into autosampler vials for analysis. The HPLC system consisted of a Beckman model 501 autosampler, Beckman model 110A pump, temperature controlled column (Eldex), Variable Wavelength Detector (detection at 210 nm, Waters and Assoc.), and integrating recorder (Hewlett-Packard, 3390). The column used was a Bio-Rad HPX-86 organic acids packed column. The column temperature was controlled at 45° C. The eluant was 0.01 N sulfuric acid in distilled water, which was filtered (0.2 micron) and degassed before use. The flow rate of eluant was maintained at 0.5 mL/min. Samples were analyzed in conjunction with high purity standard mixtures of organic acids (Supelco). Analysis by HPLC identified both non-volatile and volatile organic acids and, therefore, served as a backup to the GLC analysis.

Solids analysis of digester effluents was conducted using 1.0-g weight tins. Twenty to thirty grams of sludge sample were loaded into the preweighted tin and dried 48 h at 45°-50° C. The tin/dry samples were cooled to room temperature in a laboratory desiccator and weighed using a Sartorious balance (model 1684MB). Percent solids in the digester sludge were calculated on a weight/weight basis.

EXAMPLE 7

Gas Analysis

Production of biogas from high solids reactors was monitored on a daily basis (in conjunction with batch feeding) using calibrated water displacement reservoirs.

Biogas produced in the various digesters was analyzed for methane and nitrogen composition by gas chromatography. A Gow-Mac (model 550) gas chromatograph equipped with a thermal conductivity detector and integrating recorder was used. The injection port, oven and detector were maintained at 100°, 90°, and 110° C., respectively. Helium served as a carrier gas. The chromatograph was calibrated with high purity gas standards (Matheson).

EXAMPLE 8

Microbiological Analysis

Observation of sludge samples from high solids reactors was conducted using wet-mount slide preparations with a Nikon Labophot microscope equipped with phase contrast/epifluorescent illumination and 1000× power. Methane-producing bacteria were detected by their unique autofluorescence upon excitation by the epifluorescent light source (narrow band width centered at 420 nm).

EXAMPLE 9

Horsepower Requirements

Initial testing of horsepower requirements for mixing of MSW milled to two different sizes employed various blade configurations. The effectiveness of mixing of the material was also assessed. In general, the curved and straight solid blade designs required the most horsepower for mixing (see Table 1).

TABLE 1

Average Horsepower Requirement for Mixing of 30% Solids MSW in the High Solids Reactor Using Different Agitator Blade and Milled MSW Meal

| Agitator | Mixing Speed | Blade-Vessel Clearance 2 mm | 5 mm | 10 mm |
|---|---|---|---|---|
| 1 mm MSW Meal | | | | |
| Straight | 1.5 rpm | 0.011 | 0.009 | 0.007 |
| | 12 rpm | 0.025 | 0.015 | 0.010 |
| Curved | 1.5 rpm | 0.011 | 0.009 | 0.007 |
| | 12 rpm | 0.025 | 0.020 | 0.012 |
| Rake | 1.5 rpm | 0.005 | 0.004 | 0.004 |
| | 12 rpm | 0.007 | 0.010 | 0.017 |
| ⅛ in. MSW Meal | | | | |
| Straight | 1.5 rpm | 0.020 | 0.015 | 0.005 |
| | 12 rpm | 0.045 | 0.034 | 0.030 |
| Curved | 1.5 rpm | 0.014 | 0.009 | 0.005 |
| | 12 rpm | 0.039 | 0.030 | 0.025 |
| Rake | 1.5 rpm | 0.009 | 0.011 | 0.011 |
| | 12 rpm | 0.007 | 0.011 | 0.020 |

The more coarsely MSW (⅛ in.) required more horsepower than the finer milled material (1 mm). As the blade-vessel clearance was reduced, the horsepower required for mixing increased; this was due to pinching of the MSW in the reactor at the blade vessel edge. During extended operation of the solid blades, the volume of MSW on the sides of the blades became uneven because of variations in the exact blade-vessel clearances of the two edges of the blades. This asymmetry led to large pressure variations on the hydraulic motor and translated into large horsepower swings.

The mixing of a 30% solids MSW material with the solid base configuration also formed balls of material because of the MSW tumbling down the face of the solid blade. This clumping of material within the reactor resulted in unsatisfactory mixing performance with both of the solid blade designs. The rake blade configuration (essentially a rod with end wiper) did not form clumps of material in the reactor, but in comparison to the rod blade configuration, required more horsepower for mixing (see Table 2).

TABLE 2

Average Horsepower Requirements for Mixing of 1/-In. Milled MSW at 1.5 rpm and 30% Solids MSW in the High Solids Reactor Using Modified Rake Type Agitator Blades

| Agitator | 5 mm Blade-Vessel Clearance |
|---|---|
| 180° Rake | 0.011 |
| 120° Rake | 0.011 |
| 120° Rod | 0.006 |
| 120° Teflon Rod | 0.004 |
| 120° Opposing Teflon Rod | 0.002 |
| 90° Opposing Teflon Rod | 0.002 |

During the first inoculated run of the high solids reactor with the rod type blade, material adhered to the rods and hub. After Teflon coating of the rods and hub, no significant adherence of the material occurred. The Teflon coating also resulted in a lower horsepower requirement as compared to a Nonteflon-coated rod blade. The angle and alignment of the rods also affected the required horsepower and effectiveness of mixing. In general, changing the angle from 180° to 120° and to 90° and opposing the rods rather than aligning each row, resulted in less lifting of material and more even mixing of solids. Less lifting of the material resulted in a lower horsepower requirement and dampened the high and low horsepower spikes. As a result, the 90° Teflon-coated, opposed-rod blade configuration was used in the inoculated solids, digestion experiments.

EXAMPLE 10

Optimization of Parameters

The first operational run of the high solids reactor was initiated by additional of 1 kg of ⅛-in. hammer milled MSW to the reactor, which was outgassed with oxygen-free nitrogen for 2 h. Anaerobically, 3 L of sludge was added. Over a 4-h period, the MSW became uniformly moist, and gas production occurred. After 3 d, the pH dropped to 5.13, and analysis of the gas produced indicated no methane production. The determination of minor concentrations of oxygen in the gas phase indicated insufficient outgassing during start-up, and the fermentation was terminated.

In run 2, the reactor was initiated as in run 1, but with more extensive outgassing to remove oxygen. The total gas production quickly peaked to about 6750 mL/d and dropped off dramatically to less than 1000 mL/d along with a pH drop from over 7 to about 5.5. With the exception of lactic acid, the level of organic acids increased in general to a cumulative acid level of approximately 0.2M. Without pH control, the pH fell to 5.25 after 7 d of operation, and the fermentation was terminated.

In fermentation run 3, the reactor was initiated as in run 1 and 2, but with outgassing overnight to more completely remove oxygen entrapped in the dry MSW material. Again, gas production peaked sharply then fell off, with pH also falling sharply. The pH shifts were adjusted using 0.5% urea (final concentration in reactor) and later sodium carbonate. It was apparent that while the urea effectively buffered the pH shift, the effects of the added concentration were for a time inhibitory to the microbial population. The latter addition of sodium carbonate (6 g/L) demonstrated a less severe effect, and gas production stayed stable for several days at about 4000 mL/d with pH kept at 7.5. The level of organic acids continued to increase during the fermentation, especially for acetic acid with a final total organic acid level of approximately 0.175 M, of which 80% was acetic. The fermentation was terminated because of the excessive levels of acetic acid present.

The high initial levels of acids in the high solids reactor runs indicated the need to enhance the population of acetogens and methanogens in the digester sludge used to inoculate the reactor. A fermenter was initiated to produce an enhanced acetogen/methanogenic culture by controlled continuous addition of organic acids. The acids and their relative concentration were determined by the final acid pools for high solids runs 2 and 3. The gas production for this microbial consortium producing fermenter rose quickly to about 5000 mL/d, leveling off slowly to about 3000 mL/d. Propionic acid levels were fairly stable at about 125–150 mM. Butyric and acetic acid levels were stable at about 50–75 mM. The resulting microbial population consisted of many different rod forms and autofluorescing rods and large clumps of sarcina under epifluorescent microscopy. The cells from this fermenter were harvested, refrigerated for storage, and added to the digester sludge upon inoculation of subsequent high solids runs.

High solids run no. 4 was initiated with addition of 3.6 kg dry MSW. The MSW was mixed while outgassing overnight with oxygen-free nitrogen gas. A total of 7.4 L of liquid was added of which 6.4 L was digester sludge and 1 L was nutrient solution. The nutrient solution contained 8 g yeast extract, 50 mM $K_2HPO_4$, 18 g urea, and 120 mL of 10× trace mineral solution (Balch et al., supra). The operation was severely unstable requiring substantial pH adjustments, and the contents were diluted to 12% solids by addition of digester sludge to maintain the fermentation. The fermentation then became stable, and with addition of the nutrient solution, most parameters stabilized. Gas production between 4000 and 6000 mL/d was achieved.

The continuous run depicted in FIG. 4 has been described above and with gradual solids buildup has resulted in stable long-term high rates of gas production.

The results have shown in initial fermentation runs with the high solids that initiating the fermentation at the high solids level by adding a great excess of substrate results in a severely unstable fermentation. Apparently, this problem is due to extremely rapid buildup of acids with the high substrate concentration before enough methanogens are available to use the acids. To achieve a balanced digested consortium, adaption to the high solids level by gradual dry substrate addition is required. After this balanced population is attained, high solids fermentation occurs stably. In addition, several agents that may be useful for pH adjustment during the fermentation were identified and tested, and the relative concentrations of agents were determined that would not substantially reduce gas production.

Having observed the principles of this invention, as described above, it will be appreciated that particular manufactured components and optimizations of process parameters necessary to practice the invention are within the knowledge and capabilities of persons ordinarily skilled in these relevant arts. Therefore, for the sake of brevity and clarity, the specific details thereof require no further comment.

The foregoing is considered as illustrative only of the principles of the invention. Further, because numerous modifications and changes will readily occur to those skilled in the art, it is not desired to limit the invention to the exact construction and operation shown and described, and accordingly, all suitable modifications and equivalents may be resorted to falling within the scope of the invention as defined by the claims that follow.

The embodiments of the invention in which an exclusive property or privilege is claimed are defined as follows:

1. A fermentation reactor designed for fermentation of materials comprising greater than about 10% solids, said reactor comprising (a) a horizontal cylindrical vessel;

(b) a rotatable shaft extending along the central axis of said vessel; wherein said shaft including rigidly attached mixing members capable of stirring said materials; wherein said mixing members comprise rods which are perpendicular to said shaft;

(c) motor means for rotating said shaft in said vessel.

2. The reactor of claim 1 wherein said mixing members are disposed in staggered rows around said shaft.

3. The reactor of claim 1 wherein said mixing members are stick-resistant.

4. The reactor of claim 3 wherein said mixing members are comprised of TEFLON coated metal.

5. The reactor of claim 2 wherein said mixing members are disposed in four rows along said shaft.

6. The reactor of claim 5 wherein said rods are disposed at about 90° angles from their next adjacent rod(s).

7. The reactor of claim 1, wherein said mixing members are cylindrical rods attached along the length of said shaft, wherein said rods have a diameter in the range of about 0.25 to 0.5 inch; and wherein said rods are parallel to each other.

8. A fermentation reactor for anaerobic digestion of solid wastes for gas production comprising (a) a horizontal cylindrical vessel;

(b) a rotatable shaft extending along the central axis, said shaft including rigidly attached, stick-resistant rods spaced symmetrically therealong, each disposed at a 90° angle from its next adjacent rod(s); wherein said rods are perpendicular to said shaft;

(c) motor means for rotating said shaft in said vessel.

9. A fermentation reactor in accordance with claim 8, wherein said vessel includes a port for feeding said wastes to said vessel; wherein said rods have a circular cross-section; and wherein said rods are disposed in staggered rows along the length of said shaft.

* * * * *